United States Patent
Vija et al.

(10) Patent No.: US 10,925,564 B2
(45) Date of Patent: Feb. 23, 2021

(54) MEDICAL IMAGING SYSTEM WITH RANGE IMAGING-BASED CONTROL

(75) Inventors: Alexander Hans Vija, Evanston, IL (US); Ansgar Graw, Chicago, IL (US); Dennis Steibel, Jr., Lake Zurich, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 1195 days.

(21) Appl. No.: 13/451,579

(22) Filed: Apr. 20, 2012

(65) Prior Publication Data

US 2013/0281818 A1 Oct. 24, 2013

(51) Int. Cl.
*A61B 6/00* (2006.01)
*A61B 6/10* (2006.01)
*A61B 5/055* (2006.01)
*A61B 6/03* (2006.01)

(52) U.S. Cl.
CPC .............. *A61B 6/467* (2013.01); *A61B 5/055* (2013.01); *A61B 6/032* (2013.01); *A61B 6/037* (2013.01); *A61B 6/102* (2013.01); *A61B 6/5294* (2013.01); *A61B 6/548* (2013.01)

(58) Field of Classification Search
CPC ........... A61B 5/00; A61B 5/055; A61B 6/467; A61B 6/548; A61B 6/5294; A61B 6/032; A61B 6/102; A61B 6/037

USPC ......................................... 600/407, 410, 425
See application file for complete search history.

(56) References Cited

U.S. PATENT DOCUMENTS

| | | | |
|---|---|---|---|
| 6,272,368 B1* | 8/2001 | Alexandrescu | 600/407 |
| 6,937,696 B1* | 8/2005 | Mostafavi | A61B 5/113 378/65 |
| 7,428,296 B2 | 9/2008 | Bernhardt et al. | |
| 7,857,512 B2 | 12/2010 | Camus | |
| 2008/0031413 A1* | 2/2008 | Bouvier | A61B 6/102 378/63 |
| 2008/0253519 A1* | 10/2008 | Bonfiglio | A61B 6/00 378/65 |
| 2009/0015669 A1* | 1/2009 | Klingenbeck-Regn | A61B 6/102 348/142 |

* cited by examiner

*Primary Examiner* — Peter Luong

(57) ABSTRACT

A system includes a scanner configured to generate scan data of a patient volume or area, a processor configured to implement control operations, the control operations being directed to acquisition of the scan data or to processing of the scan data, and a monitoring system including a range imaging camera positioned for a field of view such that the monitoring system is configured to capture spatial data indicative of movement of an object spaced from the scanner. The processor is configured to implement an adjustment in the control operations based on the spatial data.

20 Claims, 3 Drawing Sheets

MEDICAL IMAGING SYSTEM WITH RANGE IMAGING-BASED CONTROL

BACKGROUND

The present embodiments relate to medical imaging systems.

Medical imaging procedures often include a considerable number of scans of a patient. For example, medical imaging procedures directed to computed tomography (CT) reconstruct a three-dimensional image from multiple two-dimensional scans.

A patient is typically directed not to move during medical imaging procedures. The patient is often supported on a bed. Lying on the bed may help the patient maintain a stationary position during the imaging procedure. Otherwise, patient movement may complicate the image reconstruction and other data processing procedures implemented to integrate the scan data from the scans.

Patient motion is tracked during some medical imaging procedures. For instance, the respiration of the patient moves organs or other tissue of interest. To account or compensate for respiratory motion, chest volume is often detected using sensors, such as strain gauges, placed on the patient's chest. The sensors typically measure pressure changes to provide an indication of the respiratory motion of the patient. The sensors and other apparatus worn by the patient may complicate implementation of the imaging procedure.

Respiratory motion and other movement of the patient may be tracked via comparison of fiduciary marks in sequential images. The comparison may be suitable for aligning the sequential images, but may not yield sufficient information for other purposes.

Some medical imaging systems include a patient detection pad to act as a safety mechanism. In addition, some systems include a light curtain to act as a rough indicator of the patient contour and to also supply patient detection status. Analysis of the data provided by these sources may be too limited for use beyond the dimensions and reach of the pad and/or light curtain.

BRIEF SUMMARY

By way of introduction, the preferred embodiments described below include methods, systems, and computer-readable media for controlling a scanner of a medical imaging system. The scanner is controlled based on spatial data captured by, or received from, a range imaging camera. The range imaging camera is used to control or operate in conjunction with the scanner.

In a first aspect, a system includes a scanner configured to generate scan data of a patient volume or area, a processor configured to implement control operations, the control operations being directed to acquisition of the scan data or to processing of the scan data, and a monitoring system including a range imaging camera positioned such that a field of view of the range imaging camera includes the scanner. The monitoring system is configured to capture spatial data indicative of movement of an object spaced from the scanner. The processor is configured to implement an adjustment in the control operations based on the spatial data.

In a second aspect, a method is provided for controlling a medical imaging system, the medical imaging system comprising a scanner configured to generate scan data of a patient volume or area. The method includes capturing, with a range imaging camera, spatial data indicative of movement of an object adjacent to the scanner, determining an operational procedure for implementation based on the spatial data, the operational procedure being directed to acquisition of the scan data or processing of the scan data, and directing the implementation of the operational procedure.

In a third aspect, a non-transitory computer program product includes a computer-readable medium encoded with computer-readable instructions that, when executed by a processor, direct the processor to receive spatial data from a range imaging camera having a field of view such that the spatial data is indicative of movement of an object adjacent to the scanner, the scanner being configured to generate scan data of a patient volume or area, access a memory in which model data for the object is stored, and determine an operational procedure for implementation based on the spatial data, the operational procedure being directed to acquisition of the scan data or processing of the scan data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
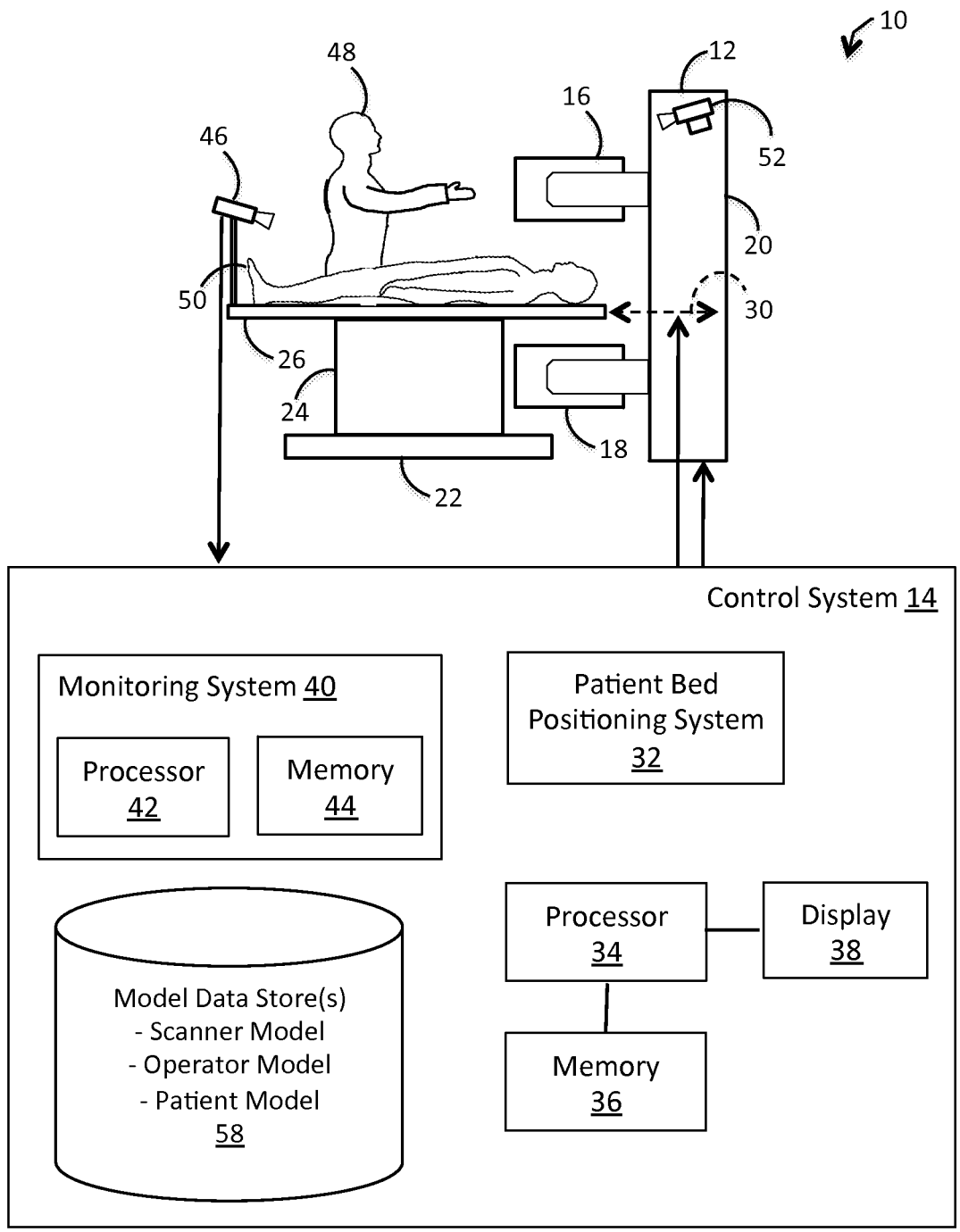
FIG. 1 is a schematic diagram of a medical imaging system having a monitoring system according to one embodiment.

Methods, computer program products, and systems that use one or more range imaging cameras to support the operation of a medical imaging system are described. Data captured by the range imaging cameras may be used to support and control acquisition of scan data by a scanner of the medical imaging system. For example, the disclosed methods, computer program products, and systems may support processing (e.g., correction) of the scan data in connection with a data reconstruction procedure. The disclosed methods, computer program products, and systems may thus be used to address the degradation of scan data that may result from patient motion. For example, the data may be used to detect and measure (e.g., quantify) magnitude, direction, and/or other characteristics of the patient motion. The disclosed methods, computer program products, and systems may be configured to use the quantification of the patient motion to correct or compensate for such motion. Respiration motion is one example of patient motion. In respiration motion, chest movement may be detected and quantified without the use of respiration sensors and without the use of fiduciary marks. The correction or compensation may be direct or indirect (e.g., image-based correction).

The disclosed methods, computer program products, and systems may alternatively or additionally provide touch-less or touch-free configuration and/or control of the medical imaging system. The medical imaging system may be set up, initialized, or otherwise configured for a scan procedure through one or more gestures made by an operator and captured by the range imaging camera(s). The gestures may establish one or more parameters of the scan procedure. The operator of the medical imaging system may be identified via the range imaging camera as the individual capable of providing gestures for operational control.

Capturing gestures to control the medical imaging system may be more intuitive and/or user friendly than control techniques that rely on controller devices, such as a handheld remote control device. For instance, the disclosed methods, computer program products, and systems may support control gestures that are much easier for an operator to execute than conventional control techniques. Such conventional control techniques may involve locating and activating specific buttons on handheld controller devices during operation or configuration of the medical imaging system. The control of the medical imaging system through captured gestures may also minimize or avoid the use of handheld and other controller devices of the medical imaging system. Such controller devices are subject to wear and other damage. Cordless controller devices may be misplaced or otherwise inaccessible during operation. The reliability of the medical imaging system may thus be improved.

The operational control supported by the range imaging camera data is not limited to touch-free or gestured control. The operation of the medical imaging system may be automatically controlled in response to the detection of a foreign object that presents a potential hazard. For example, scan procedures may be stopped upon detection of a possible collision due to motion or operation of the medical imaging system. The collision may involve any object foreign to the medical imaging system, including, for instance, an operator, a patient, or another device or system. The data provided by the range imaging camera may be used to predict future movement (e.g., of the foreign object), as well as determine when such collisions are likely to occur via, for instance, a likelihood of collision determination.

The disclosed systems may include a monitoring system to generate spatial and/or range data for a variety of objects foreign to the medical imaging system. The spatial and/or range data may be indicative of the distance from one or more cameras (e.g., range imaging cameras) to the object. The spatial and/or range data may be useful for defining the geometry or shape of the object. With the object geometry established, the spatial and/or range data may provide feedback on the direction, speed, and other characteristics of the movement of the object. The object may be tracked relative to the medical imaging system.

The disclosed methods, computer program products, and systems may be useful with a wide variety of medical imaging systems. Although described below in connection with an X-ray computed tomography (CT) system, the configuration of the imaging system may vary. For example, the disclosed detectors may be integrated into a magnetic resonance imaging (MRI) system, a positron emission tomography (PET) system, or a single-photon emission computed tomography (SPECT) system. The medical imaging systems need not include components that move, such as C-arm X-ray systems. The disclosed methods, computer-readable media, and systems may be used with any now known or future developed nuclear medicine tomography or other imaging systems. Still other example systems may include multiple scanners in, for instance, a multi-modal imaging system, such as a magnetic resonance (MR)-PET system.

FIG. 1 depicts a medical imaging system 10 constructed in accordance with one embodiment. The medical imaging system 10 includes a scanner 12 and a control system 14 configured to direct the scanner 12. The medical imaging system 10 may include additional systems, devices, or components. For example, the medical imaging system 10 may include one or more power supplies or other support equipment, such as communications systems, image processing systems, tomography generation systems, and user interface systems.

The scanner 12 is configured to generate scan data of a patient volume or area. The scanner 12 may include any data acquisition unit for generating such scan data. In this embodiment, the scanner 12 is an X-ray scanner having a source 16 and a detector 18 (or receiver). The scanner 12 may be a PET scanner, an MRI scanner, an X-ray scanner, a SPECT scanner, and/or any other now known or hereafter developed scanner. The scanner 12 may include multiple data acquisition units integrated to any desired extent. For example, the scanner 12 may be a multi-modal data acquisition unit. The scanner 12 may have any number of sources 16 and detectors 18. For example, in non-X-ray embodiments, the scanner 12 may include zero sources and multiple detectors 18 arranged in a ring or other arrangement about the patient.

One or both of the source 16 and the detector 18 may move during operation. For example the source 16 may be repositioned vertically relative to the patient. In other examples, the source 16 and/or detector 18 translate in more than one dimension (e.g., laterally as well as vertically), rotate in one or more dimensions (e.g., as in a C-arm system), or move in any other desired manner.

The scanner 12 includes a gantry 20 that supports the source 16 and the detector 18. The gantry 20 may be stationary or mobile. Any number of data acquisition components of the scanner 12 may be supported or carried by the gantry 20. The gantry 20 includes a housing that encloses such data acquisition components of the scanner 12. In some examples, the source 16 and the detector 18 are housed within the gantry 20. One or more components of the control system 14 may also be housed in the gantry 20. The gantry 20 may have an opening in which the patient is disposed. For example, the gantry 20 may have a toroid shape.

The medical imaging system 10 includes a patient bed assembly 22 with a base 24 and a platform 26 supported by the base 24. One or more of the components of the patient bed assembly 22 may be movable to position the patient for the scan procedure. For example, the platform 26 may move in a direction 30 toward or through the gantry 20 as shown. Alternatively or additionally, one or more components of the base 24 may move relative to the gantry 20 or other component of the system 10, such as the source 16 and/or the detector 18.

The disclosed methods, computer program products, and systems are not limited to use with medical imaging systems having a patient bed. For example, the medical imaging system 10 may be configured for scan procedures in which the patient is standing or sitting. The nature, construction, and other characteristics of a base, a platform, or other component of the system 10 involved in positioning the patient (or a portion of the patient) may thus vary.

The control system 14 may include a patient positioning system 32 to control the positioning of the patient. In this example, the patient positioning system 32 is a patient bed positioning system configured to control the movement of the platform 26 along the direction 30. One or more modules, components, or other aspects of the patient positioning system 32 may be disposed in the gantry 20. The control system 14 may be integrated with the scanner 12 to any desired extent.

The control system 14 includes a processor 34 configured to implement control operations, a memory 36 in communication with the processor 34, and a display 38 controlled by the processor 34. The control operations are directed to acquisition of the scan data by the scanner 12 and/or to processing of the scan data. For example, the control operations may include directing the patient positioning system 32 to re-position the patient in accordance with a scan procedure. The control operations may include configuring the scanner 12 for the scan procedure. For example, the control operations may include facilitating the selection and/or configuration of the scan procedure by an operator. The control operations may alternatively or additionally include directing one or more components of the scanner 12 to conduct the scan procedure. Conducting the scan procedure may include directing the movement of such component(s) of the scanner 12 by, for instance, sending instructions or other control signals to the scanner 12. Another example is control of intensity, amplitude, aperture, steering, collimation or other characteristic of the applied energy and/or receipt of the responsive signals.

The control system 14 also includes a monitoring system 40. In this example, the monitoring system 40 includes a processor 42 and a memory 44, each of which may be located remotely from the scanner 12 with any one or more other electronics components of the control system 14. The monitoring system 40 is configured to capture and/or generate spatial data representative of a two-dimensional image and a distance or range from a specific point, such as a point on the scanner 12. The spatial data of successive frames may be processed by the processor 42 or another processor via a difference, tracking, or other function, algorithm, or procedure to provide a representation of movement. In one example, a difference imaging procedure and/or a filtering procedure may be implemented. The algorithm may vary based on the nature of the spatial data, the nature of the scanner 12, and/or other factors. For instance, the spatial data may vary considerably based on whether the scanner 12 is configured for CT scans, MR scans, and/or SPECT scans. The spatial data may be indicative of relative movement between the scanner 12 and one or more objects spaced from or adjacent to the scanner 12. Such relative movement may include or involve movement by the object(s) relative to the scanner 12, movement by a component of the scanner 12 relative to the object(s), or movement by both the object(s) and the component of the scanner 12. The spatial data may include data indicative of the spatial position of such objects at a specific time or over a time period.

The monitoring system 40 includes a range imaging camera 46, such as a time-of-flight camera, to capture data. The range imaging camera 46 may generate the spatial data, and/or generate raw data used to generate the spatial data. The spatial data may include or be representative of distance or range data indicative of the distance between the object and the range imaging camera 46.

The nature of the objects may vary. The object may be a person, such as an operator 48 of the medical imaging system 10 or a patient or subject 50 lying on the platform 26. Other examples of objects foreign to the scanner 12 include equipment, machines, or other devices.

The range imaging camera 46 is positioned for a field of view such that the monitoring system 40 is configured to capture the spatial data indicative of the relative movement. In this example, the range imaging camera 46 is mounted on an end of the platform 26 of the patient bed assembly 22. The end is spaced from the gantry 20 such that the field of view includes all or a portion of the operator 48, the patient 50, the source 16, and the gantry 20. Fewer, additional, or alternative components of the scanner 12 may be within the field of view. The movement of any of the above-described components of the scanner 12 may be captured by the range imaging camera 46. Fewer, additional, or alternative objects foreign to the scanner 12 may be within the field of view.

The field of view of the range imaging camera 46 may vary considerably. The field of view may include the scanner 12, such as one or more components of the scanner 12. Any portion, fraction, or aspect of the scanner 12 may be within the field of view of the range imaging camera 12. The spatial data may thus include data indicative of the position of a movable component of the scanner 12. Alternatively or additionally, the position of the scanner 12 or movable component thereof is determined by the processor 34 and/or the processor 42. In these cases, the field of view of the range imaging camera 46 need not include the component(s) of the scanner 12 from which the foreign object is spaced. Nonetheless, the processor 34 or the processor 42 may be able to calculate an indication of the scanner position(s) based on model data indicative of the scanner 12. Further details regarding the use of such model data are provided below.

The range imaging camera 46 is any type of camera or image data acquisition device or system configured to capture and/or generate spatial data indicative of the spatial position of the foreign object. The spatial position may be a relative position based on, for instance, a non-fixed reference frame of the range imaging camera 46 and/or of the scanner 12. Alternatively, the position may be an absolute position in a fixed reference frame of, for instance, the range imaging camera 46, the monitoring system 30, or the scanner 12. The position may thus be relative to the range imaging camera 46, one or more components of the scanner 12, or any other component of the medical imaging system 10.

The spatial data may include range data indicative of the range or distance between the foreign object and the range imaging camera 46. To generate the range data, the range imaging camera 46 may be configured to transmit an infrared (IR) signal, such as an IR laser signal, detect reflections (e.g., backscattering) of the IR signal, and determine the time-of-flight of the IR signal. The wavelength of the light emitted and detected by the range imaging camera 46 may vary, and need not be in the IR wavelength range. The light may be coherent or non-coherent. Other techniques may be used. For example, the range imaging camera 46 may use other types of signals to generate the range data, such as structured light signals generated by a three-dimensional structured light scanner.

The range imaging camera 46 may include various types of range cameras or other range detection devices. In one example, the range imaging camera 46 is configured as a light detection and ranging (LIDAR) device or system, or other type of time-of-flight device. The range imaging camera 46 is not limited to sensing distance or range via time-of-flight techniques. For example, the range imaging camera 46 may utilize stereo triangulation, interferometry, and other techniques.

In some embodiments, the range imaging camera 46 includes one or more commercially available components, such as one or more lasers and/or detectors (e.g., solid state photodetectors). Alternatively, the range imaging camera 46 is a commercially available integrated device including such components. For example, a variety of commercially available time-of-flight cameras may be used. In some embodiments, the range imaging camera 46 is capable of resolving motion differences on the order of 5 mm over the distances typically encountered with, or presented by, the medical imaging system 10 and given a suitable temporal sampling rate for the camera. One or more other components of the monitoring system 40 may also be commercially available components. Such cameras and monitoring system components may be commercially available in connection with gaming devices or systems, such as the Kinect™ motion sensing input device available from Microsoft Corporation.

The spatial data generated and/or captured by the range imaging camera 46 may be indicative of the object position over time. The range imaging camera 46 may be configured as a four-dimensional camera. Alternatively, the spatial data may be aggregated or otherwise processed by the processor 42 to provide the indication of object position over time.

The monitoring system 40 may include any number of range imaging cameras, which need not be mounted on a movable component of the scanner 12. Multiple cameras may minimize or avoid shadowing. The range imaging cameras may be stationary or non-stationary relative to the scanner 12 or a component thereof. The example of FIG. 1 includes an additional range imaging camera 52 fixedly mounted on the gantry 20. A gantry mount is one example of a stationary mounting location to support a fixed reference frame. In contrast, the range imaging camera 46 has a non-fixed reference frame. The range imaging camera 46 is non-stationary with respect to some components of the scanner 12 (e.g., the gantry 20) due to being mounted on the platform 26.

The location of the range imaging cameras 46 and 52 may vary from the example shown. For example, one or more range imaging cameras may be mounted on a wall, ceiling, or other structure in the vicinity of the scanner 12. Different mounting positions may provide multiple, differing fields of view to capture spatial data for different foreign objects. Alternatively or additionally, the spatial data may be directed to the same object. For example, the range imaging camera 52 may provide spatial data to the processor 42 of the monitoring system 40 for aggregation or other processing in conjunction with the spatial data provided by the range imaging camera 46. The aggregated data may thus be indicative of the position and/or movement of the same foreign object.

Each range imaging camera 46, 52 may include an optical camera configured to provide additional or alternative resolution for the spatial data. For example, data generated by the optical camera may be processed to improve the resolution of the range data in one or more dimensions other than the dimension of the range data. The data from the optical camera may be used to support the implementation of adaptive filtering, image restoration, and/or other techniques.

The processor 34 is configured to implement an adjustment in the operational control of the scanner 12 based on the spatial data provided by the range imaging cameras 46, 52 and/or the monitoring system 40. The operational control adjustment may occur before the scan procedure is implemented, during the scan procedure, or after the scan procedure is completed. Operational control adjustments before the scan procedure may involve control operations directed to, for instance, system setup, scan procedure setup or definition, and any other configuration procedure in which the operator 48 may provide an input or command. Operational control adjustments during the scan procedure may involve stopping the movement of the scanner 12 to avoid a collision with a foreign object and/or generating a warning, alert, or other announcement regarding the possibility of the collision. Operational control adjustments after the scan procedure may involve compensation for patient motion during the scan procedure. For example, the magnitude and direction of external patient movement may be captured to either direct scan data corrections or to assist in image-based motion correction.

The spatial data may be indicative of gestures by the operator to facilitate touch-less or touch-free control of the scanner 12. The foreign object monitored by the monitoring system 40 may thus be a hand, arm, or other body part of an operator of the scanner 12. The processor 42 and/or the processor 34 may implement one or more routines to analyze the spatial data to capture or recognize a gesture made by the operator relative to a reference frame of the scanner 12. The gesture is indicative of an operational command. Once the gesture is recognized, the processor 34 may adjust the operation of the scanner 12 by implementing the operational command associated with the gesture.

In some embodiments, gesture control may include a sequence of gestures. The use of a sequence may be one of a number of characteristics of the gestures configured to provide safety and reliability during system operation. For example, gestures may be defined not only for specific system commands (e.g., operational controls), but also to (i) identify an operator, (ii) enter and exit a mode (e.g., a command mode), or (iii) start (e.g., trigger) and end the command sequence. These and other gestures may be designed to be atypical or unique, but nonetheless convenient (e.g., not uncomfortable) for the operator. For instance, the gesture to identify or recognize an operator may involve the operator holding both arms straight upward. The system may be configured to track the operator (and other individuals) from that point onward and thereby distinguish the operator from other individuals present in the room. The gesture to enter a command mode or start a command sequence may involve the operator holding or maintaining a different uncommon arm position for a predetermined period of time. One example of a gesture for entering a command mode involves the operator holding both arms straight outward for a number of seconds. Such arm positions are sufficiently uncommon and the time period is long enough that accidental or unintended control adjustments may be avoided.

In some embodiments, operational commands may be recognized from gestures that begin from the command mode gesture. For example, a command to raise the height of the patient bed may start from the command mode entry position, e.g., hands straight out, and then involve the operator raising both hands upward. Another example involves the operator rotating both hands around a circle, as if turning a steering wheel, to implement a gantry rotation.

One example for exiting a command mode may involve the operator moving from one of the aforementioned gestures to point both arms straight downward. Some exit or end gestures may be configured to be easier or quicker for the operator to implement if, for instance, the gesture is directed to implementing an emergency stop. For example, an emergency stop may be implemented in response to gestures like arm waiving and rapid movement toward the system.

The gestures may be indicative of a variety of operational control adjustments. Gestures involving various operator hand movements may be used to define an imaging area or target region, begin or end the scan procedure, re-position the bed platform 26 or other component of the scanner 12, etc. Example operational controls include "start scan here," "end scan here," "bed up," "bed down," "bed in," "bed out," "rotate source left," "rotate source right," "detector in," "detector out," etc. A respective gesture for each operational command issued by the operator may be defined to establish a set of gestures to be captured or recognized by the monitoring system 40.

One or both of the processors 34 and 42 may be configured to analyze the spatial data to prevent a collision between the scanner 12 and an object foreign to the scanner 12. For example, the foreign object may be a body part of the operator, an object held by the operator, or a body part of the patient. The analysis may include a recognition or other determination that the object is indeed not part of the scanner 12. The analysis may additionally or alternatively include a determination of one or more zones of concern surrounding the scanner 12. The zone determination may be based on data indicative of where the scanner 12 will be moving. If, for instance, an operator or patient hand is disposed within a zone of concern, the processor 34 may implement an operational control adjustment that stops the motion of a component of the scanner 12 to prevent the collision.

The processor 34 and/or the processor 42 may be configured to predict future locations of the foreign object and/or the component of the scanner 12 based on the spatial data. The prediction may be useful for minimizing or avoiding collisions between the scanner 12 and such foreign objects. A prediction algorithm or procedure may be implemented based on one or models stored in a data store 58 or other memory(ies). For example, the prediction procedure may generate predictive data indicative of the position and/or movement of the operator or the patient based on an operator model or a patient model stored in the data store 58. In one embodiment, each such model may be a skeletal model to which the spatial data may be mapped. The prediction procedure may generate predictive data indicative of the position and/or movement of the scanner 12 based on a scanner model, which may include data reflective of the geometry (e.g., axes), position, and motion of one or more movable components of the scanner 12. The model data may alternatively or additionally be used by the processor(s) 34, 42 to identify an object as foreign to the scanner 12.

The processor 34 and/or the processor 42 may be configured to analyze the spatial data to generate an indication of the movement of the patient. An operational control adjustment may modify the scan data generated by the scanner 12 to compensate for the movement of the patient.

Each memory 36, 44 is a buffer, cache, RAM, removable media, hard drive, magnetic, optical, database, or other now known or later developed memory. Each memory 36, 44 is a single device or group of multiple devices. Each memory 36, 44 is shown within the control system 14, but may be outside or remote from other components of the control system 14, such as a database or PACS memory. The memories 36, 44 may be a single memory or integrated to any desired extent.

Each memory 36, 44 may store data at different stages of processing. For example, the memory 44 may store raw data from the range imaging camera 46 without further processing, and the memory 36 store raw data from the scanner 12, filtered or thresholded data prior to reconstruction, reconstructed data, filtered reconstruction data, an image to be displayed, an already displayed image, or other data. Each memory 36, 44 (or a different memory) may store data used for processing, such as storing the data after one or more iterations and prior to a final iteration in reconstruction. For processing, the data bypasses the memory 36, 44, is temporarily stored in the memory 36, 44, or is loaded from the memory 36, 44.

Each memory 36, 44 is additionally or alternatively a non-transitory computer readable storage medium storing processing instructions. For example, the memory 36, 44 stores data representing instructions executable by the programmed processor 34, 42 for reconstructing a tomography image for dynamic study and/or reconstructing an image. The instructions are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software stored or otherwise embodied on a computer-readable memory, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

Each processor 34, 42 is a general processor, digital signal processor, graphics processing unit, application specific integrated circuit, field programmable gate array, digital circuit, analog circuit, combinations thereof, or other now known or later developed device for processing emission information. Each processor 34, 42 is a single device, a plurality of devices, or a network. The processors 36, 42 may be a single processor, or be integrated to any desired extent. For more than one device, parallel or sequential division of processing may be used. Different devices making up each processor 34, 42 may perform different functions, such as one processor for filtering and/or subtracting raw data or reconstructed images. Each processor 34, 42 may include an application specific integrated circuit or field programmable gate array for performing various operations, such as iterative reconstruction. In one embodiment, the processor 34 is a control processor or other processor of a medical imaging system. The processor 34 may be a processor of a computer or workstation.

Each processor 34, 42 operates pursuant to stored instructions to perform various acts described herein. For example, the processor 42 may be operable to process data captured by the range imaging camera 46, determine the spatial data (including, for instance, the range data), identify foreign objects from the spatial data, recognize control gestures, characterize patient motion, and/or analyze the spatial data to predict the likelihood of collision. Each processor 34, 42 may be configured by code or instructions sets stored on a memory, by firmware, and/or by hardware to perform any or all of the acts described herein.

The display 38 is a CRT, LCD, plasma screen, projector, printer, or other output device for showing images generated by the medical imaging system 10. The display 38 may be used to display a user interface for controlling the medical imaging system 10. The display 38 may be an operator console for the medical imaging system 10.

Figure 2:
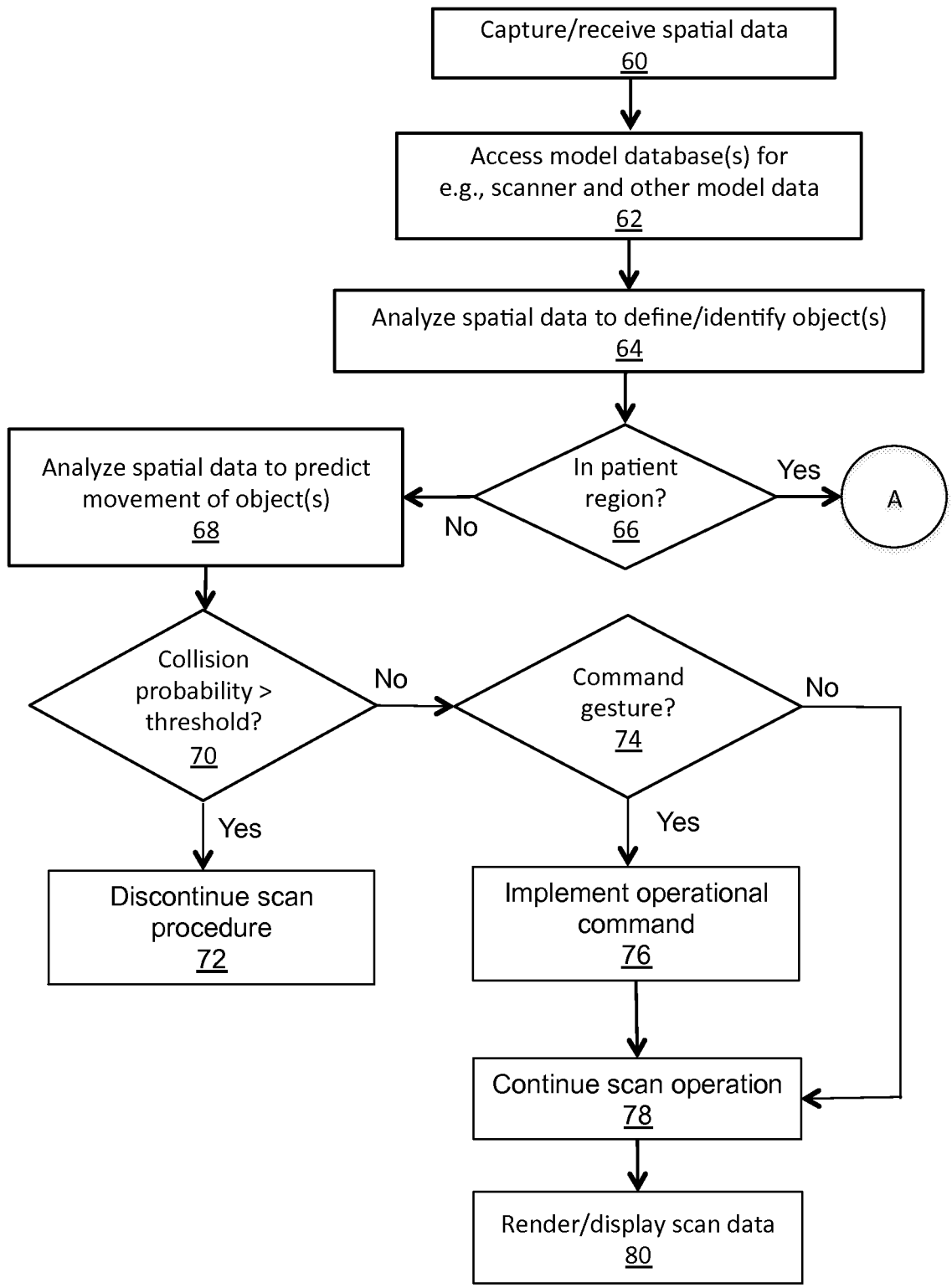
FIG. 2 is a flow diagram depicting a method of, and/or implementation of computer-implemented instructions for, controlling a medical imaging system according to one embodiment.
Figure 3:
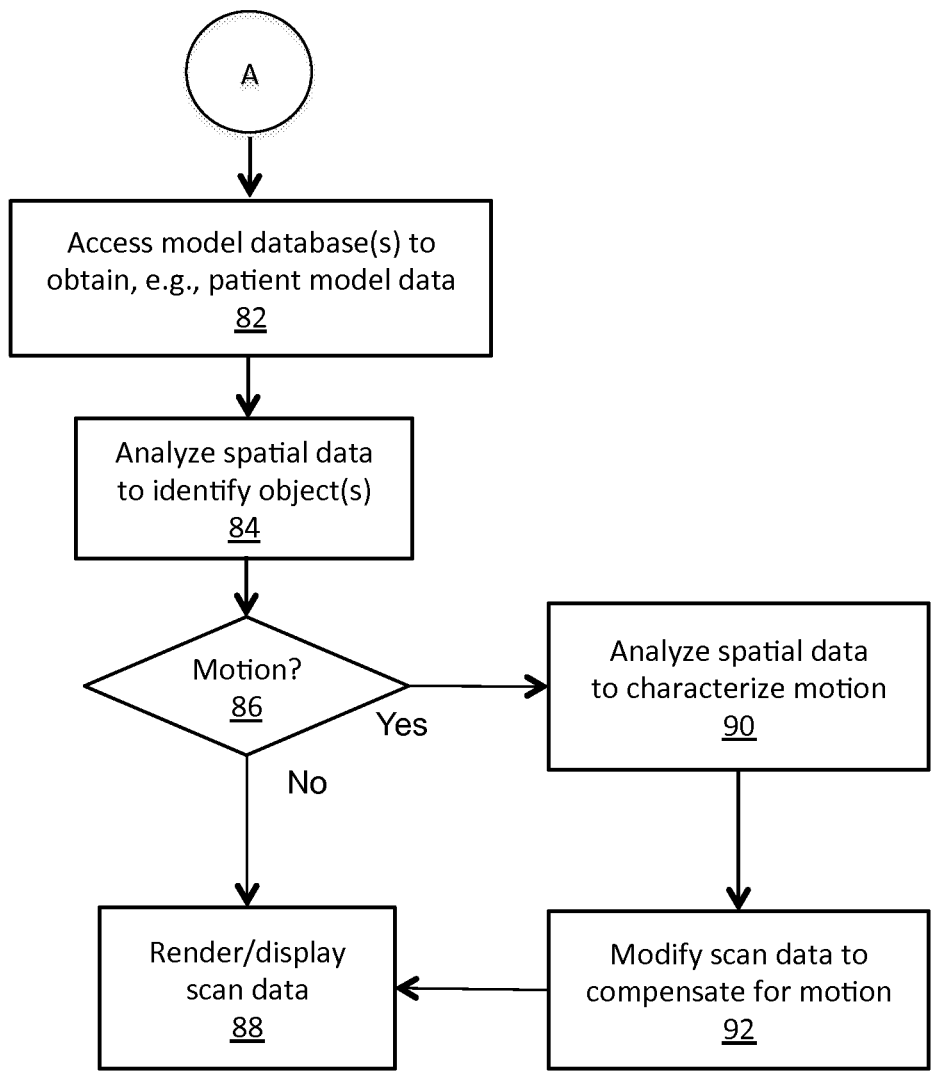
FIG. 3 is a flow diagram depicting another method of, and/or implementation of computer-executable instructions for, controlling a medical imaging system according to one embodiment.

FIGS. 2 and 3 depict one or more methods of controlling a medical imaging system having a scanner configured to generate scan data of a patient volume or area. One or both of the above-described processors, or another processor may implement the method(s). The processor(s) may be directed by computer-readable instructions executed by the processor (s). One or more of the above-described memories or other computer-readable medium may be encoded with the computer-readable instructions. In some embodiments, a non-transitory computer program product includes the computer-readable medium encoded with the computer-readable instructions. Additional, fewer, or alternative acts may be implemented by the processor(s). Additional, fewer, or alternative acts may be implemented. The acts of the methods may be implemented in an order different than the examples shown.

The method may begin with a range imaging camera capturing spatial data in act 60. Capturing the spatial data may include the implementation of one or more routines or procedures to generate spatial coordinates and other aspects of the spatial data from raw generated by the range imaging camera. Alternatively or additionally, capturing the spatial data may include the implementation of a difference or tracking algorithm, routine, or procedure that compares successive frames of the raw data or the spatial data. The spatial data may thus be indicative of movement of an object spaced from, or adjacent to, the scanner, and/or relative movement between the scanner and the object. Alternatively, the method may begin with the processor receiving the spatial data from the range imaging camera. A memory, such as a database or data store, may be accessed in act 62 to obtain model data for the scanner and/or the object. In some cases, the model data is indicative of an operator of the medical imaging system and/or the patient having the patient volume being scanned. The spatial data may be analyzed in act 64 to identify the object or objects represented by the spatial data. The model data may be used during the analysis.

The remainder of the method may be directed to determining an operational procedure for implementation based on the spatial data and directing the implementation of the operational procedure. The operational procedure may be directed to acquisition of the scan data (e.g., scanner set up) or processing of the scan data (e.g., motion compensation). FIG. 2 depicts an example of the former case, and FIG. 3 depicts an example of the latter case.

In the example shown in FIG. 2, the method determines in a decision block 66 whether any of the objects are within a range or region normally occupied by the patient. If not, control passes to act 68, in which further analysis of the spatial data may be implemented to predict movement of the object(s). One or more prediction algorithms may be implemented. For example, one prediction algorithm may be directed to predicting the future position(s) of the operator or patient based on the spatial data and a skeletal or other human model. Another algorithm may be directed to determining the future position(s) of one or more components of the scanner, such as a source, bed, etc. These positions may then be compared to determine a likelihood of collision between the object and the scanner. A decision block 70 may then determine whether the likelihood of collision exceeds a predetermined threshold. If so, then the scan procedure is stopped in act 72 to discontinue motion of a component of the scanner to prevent the collision. If not, then control may pass to another decision block 74 that determines whether the spatial data (or a derivative thereof) is indicative of a command or control gesture by the operator. If so, then the operational command indicated by the gesture is implemented in act 76. The operational command may relate to scanner configuration, scan procedure configuration, and any other control command that may be issued by the operator. If the spatial data is not indicative of a command gesture, then control passes to act 78 in which operation of the scanner may proceed or continue. Eventually, operation of the scanner continues in act 78 via, for instance, implementation of a scan procedure, from which scan data is generated for rendering or display in act 80.

The example shown in FIG. 3 may be implemented after completion of the scan procedure. The method includes accessing in act 82 a database or other data store in which model data of the patient is stored. The patient model data may be indicative of a skeletal or other human form to which the spatial data may be matched. In act 84, the spatial data is analyzed in conjunction with the model data to identify one or more objects, such as a chest of the patient. A decision block 86 may then determine whether motion has occurred. Motion may be expected during some scan procedures, such as a scan procedure directed to the chest. In other cases, motion may not be expected. If no motion is detected, then control passes to act 88 in which the scan data is rendered or displayed. If motion is detected, then the spatial data may be analyzed in conjunction with the model data to characterize the motion. For example, data indicative of the magnitude and direction of the motion may be generated for one or more regions or volumes of the patient. The scan data may then be modified in act 92 in accordance with an algorithm, process, or routine configured to correct or compensate for the motion. The corrected scan data may then be rendered or displayed in act 88.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system comprising:
   a scanner configured to generate scan data of a patient volume or area;
   a processor configured to implement control operations, the control operations being directed to acquisition of the scan data;
   a monitoring system comprising a range imaging camera positioned for a field of view such that the monitoring system is configured to capture spatial data indicative of relative movement between the scanner and an object spaced from the scanner; and
   a memory in which scanner model data for the scanner and human model data for a human skeletal model are stored, the scanner model data being reflective of geometry of the scanner;
   wherein the processor is configured to implement an analysis of the spatial data in conjunction with the scanner model data and the human model data to identify the object as a human body part foreign to the scanner based on the geometry of the scanner via the scanner model data;

wherein the processor is configured to implement an adjustment in the control operations based on the analysis.

2. The system of claim 1 wherein the scanner comprises a movable component, and wherein the range imaging camera is mounted on the movable component.

3. The system of claim 1 wherein the scanner comprises a patient bed, and wherein the range imaging camera is mounted on the patient bed.

4. The system of claim 1 wherein the scanner comprises a gantry, and wherein the range imaging camera is mounted on the gantry.

5. The system of claim 1 wherein the processor is configured to analyze the spatial data to prevent a collision between the scanner and the object, and wherein the adjustment stops motion of a component of the scanner to prevent the collision.

6. The system of claim 1 wherein:
the object is an operator of the scanner;
the processor is configured to analyze the spatial data to capture a gesture made by the operator relative to a reference frame of the scanner, the gesture being indicative of an operational command; and
the adjustment implements the operational command.

7. The system of claim 1 wherein:
the object is a patient;
the processor is configured to analyze the spatial data to generate an indication of the movement of the patient; and
the adjustment modifies the scan data based on the indication to compensate for the movement of the patient.

8. The system of claim 1 wherein the human model data comprises human skeletal model data, and wherein the processor is configured to predict further movement of the object based on the human skeletal model data and the spatial data.

9. A method of controlling a medical imaging system, the medical imaging system comprising a scanner configured to generate scan data of a patient volume or area, the method comprising:
capturing, with a range imaging camera, spatial data indicative of relative movement between the scanner and an object adjacent to the scanner;
determining an operational procedure for implementation by the medical imaging system based on the spatial data, the operational procedure being directed to acquisition of the scan data or processing of the scan data;
directing the implementation of the operational procedure; and
displaying the scan data on a display of the medical imaging system;
wherein determining the operational procedure comprises:
accessing a memory of the medical imaging system in which human model data for a human skeletal model is stored; and
analyzing the spatial data in conjunction with the human model data to identify the object as a human body part and determine the operational procedure based on the human skeletal model via the human model data.

10. The method of claim 9 wherein the object is a body part of an operator of the medical imaging system.

11. The method of claim 9 wherein the object is a body part of a patient having the patient volume.

12. The method of claim 9 wherein determining the operational procedure comprises analyzing the spatial data to prevent a collision between the scanner and the object, and wherein the operational procedure discontinues motion of a component of the scanner to prevent the collision.

13. The method of claim 9 wherein:
the object is an operator of the scanner;
determining the operational procedure comprises analyzing the spatial data to capture a gesture made by the operator, the gesture being indicative of an operational command; and
the operational procedure implements the operational command.

14. The method of claim 9 wherein:
the object is a patient;
determining the operational procedure comprises analyzing the spatial data to generate an indication of the movement of the patient; and
the operational procedure modifies the scan data based on the indication to compensate for the movement of the patient.

15. The method of claim 9, further comprising predicting movement of the object and a likelihood of collision based on the human skeletal model via the human model data.

16. The method of claim 9, further comprising:
generating predictive data indicative of movement of the scanner based on a scanner model; and
predicting a likelihood of collision based on the predictive data and the spatial data.

17. A system comprising a scanner, a processor and a non-transitory computer-readable medium encoded with computer-readable instructions that, when executed by the processor, direct the processor to:
receive spatial data from a range imaging camera having a field of view such that the spatial data is indicative of relative movement between the scanner and an object spaced from the scanner, the scanner being configured to generate scan data of a patient volume or area;
access a memory in which human model data for a human skeletal model is stored;
analyze the spatial data in conjunction with the human model data to identify the object as a human body part and determine an operational procedure for implementation by a medical imaging system, the operational procedure being directed to acquisition of the scan data or to processing of the scan data, the medical imaging system comprising the scanner; and
display the scan data on a display of the medical imaging system;
wherein the operational procedure is determined based on the human skeletal model via the human model data.

18. The system of claim 17 wherein the computer-readable instructions further direct the processor to predict further movement of the object based on the spatial data.

19. The system of claim 17 wherein:
the object is a body part of an operator of the scanner;
the computer-readable instructions further direct the processor to analyze the spatial data to capture a gesture made by the operator, the gesture being indicative of an operational command; and
the operational procedure implements the operational command.

20. The system of claim 17 wherein:
the object is a body part of a patient;

the computer-readable instructions further direct the processor to analyze the spatial data to generate an indication of the movement of the patient; and the operational procedure modifies the scan data based on the indication to compensate for the movement of the patient.

\* \* \* \* \*